United States Patent
Ma et al.

(10) Patent No.: US 7,330,264 B2
(45) Date of Patent: Feb. 12, 2008

(54) OPTICAL DETECTION DEVICE

(75) Inventors: Jang-seok Ma, Gyeonggi-do (KR); Fu Wang, Gyeonggi-do (KR); In-jae Lee, Gyeonggi-do (KR); Soo-suk Lee, Gyeonggi-do (KR); Young-nam Kwon, Gyeonggi-do (KR); Young-hoon Kim, Seoul (KR); Hui-jun Sim, Gyeonggi-do (KR); In-ho Lee, Gyeonggi-do (KR); Young-hwan Lee, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 270 days.

(21) Appl. No.: 11/071,819

(22) Filed: Mar. 3, 2005

(65) Prior Publication Data

US 2005/0195394 A1 Sep. 8, 2005

(30) Foreign Application Priority Data

Mar. 3, 2004 (KR) ...................... 10-2004-0014245

(51) Int. Cl.
*G01N 21/55* (2006.01)
(52) U.S. Cl. ...................................... 356/445; 356/311
(58) Field of Classification Search ............ 250/214 R, 250/458.1, 459.1, 467.1; 385/12, 10; 356/417, 356/311, 317, 318; 436/518
See application file for complete search history.

(56) References Cited

U.S. PATENT DOCUMENTS

| | | | |
|---|---|---|---|
| 6,289,144 B1 * | 9/2001 | Neuschafer et al. | 385/12 |
| 6,483,096 B1 | 11/2002 | Kunz et al. | 250/214 R |
| 6,979,567 B2 * | 12/2005 | Herron et al. | 435/287.1 |
| 2001/0023007 A1 * | 9/2001 | Erb et al. | 436/518 |
| 2002/0094147 A1 * | 7/2002 | Herron et al. | 385/12 |

* cited by examiner

*Primary Examiner*—Gregory J. Toatley, Jr.
*Assistant Examiner*—Tri Ton
(74) *Attorney, Agent, or Firm*—Cantor Colburn LLP

(57) ABSTRACT

An optical detection device for biochemically analyzing samples of microfluidic chips such as DNA chips or protein chips is provided. The optical detection device includes a light source for generating excitation light to excite a sample, a detection plate having an optical waveguide with the sample mounted thereon, a linear symmetry lens for shaping the excitation light into a desired shape having a uniform intensity distribution and transmitting it to the detection plate, and a detector for detecting radiation from the sample.

16 Claims, 6 Drawing Sheets

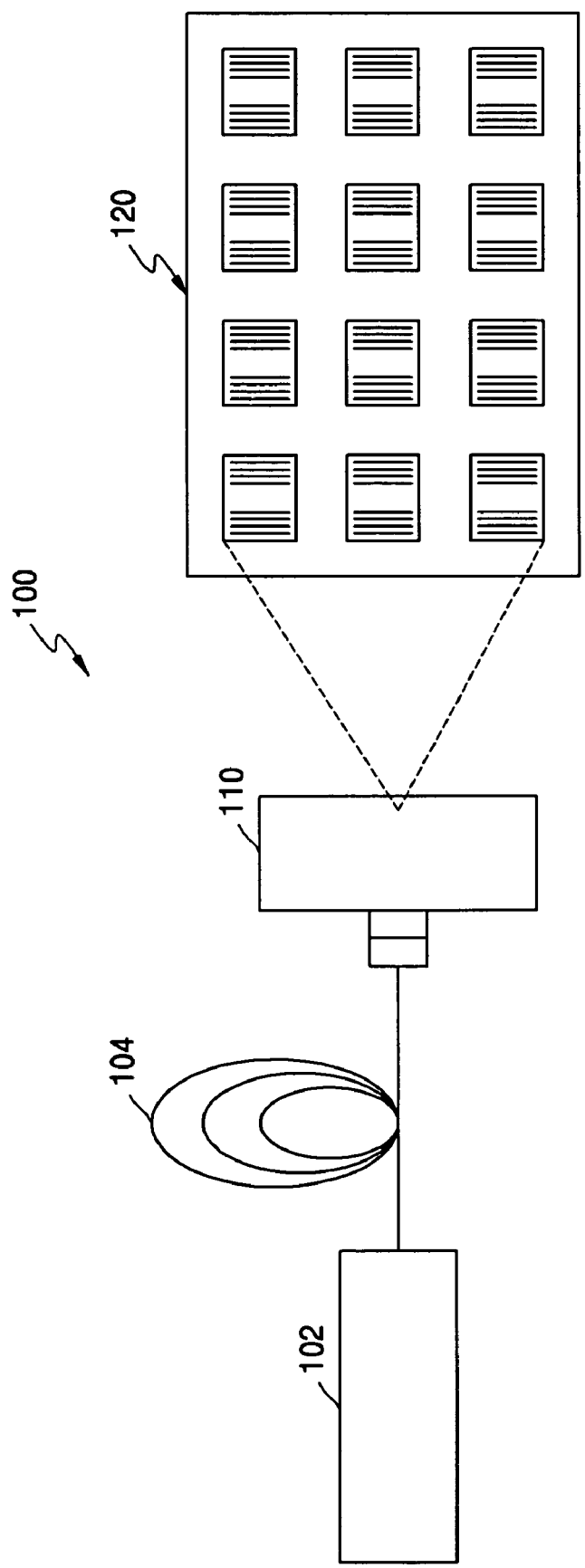

OPTICAL DETECTION DEVICE

BACKGROUND OF THE INVENTION

This application claims the priority of Korean Patent Application No. 10-2004-0014245, filed on Mar. 3, 2004, in the Korean Intellectual Property Office, the disclosure of which is incorporated herein in its entirety by reference.

1. Field of the Invention

The present invention relates to an optical detection system, and more particularly, to an optical detection device that biochemically analyzes samples of microfluidic chips such as DNA chips or protein chips.

2. Description of the Related Art

In biological diagnosis, it has recently become necessary to detect biological molecules contained in very low concentrations in samples having a very small volume. Consequently, efforts are underway to develop a highly sensitive sensor.

For biochemical applications, an optical sensor is usually preferable because it is both chemically stable and easily machined. One type of sensor suitable for biochemical application is based on a structure of illumination excitation. This sensor combines biochemical selectivity caused by recognition of molecules to be analyzed with spatial selectivity caused by evanescent field excitation.

FIG. 1 is a schematic diagram of a conventional optical detection device 10 suitable for biochemical applications.

Referring to FIG. 1, the optical detection device 10 includes an optical waveguide 11, a glass substrate 12, a first diffraction grating 13, a second diffraction grating 14, a HeNe laser 15, a lens 16, a Dammann diffraction grating 17, an achromatic cylindrical lens 18, and a mirror 19.

The optical waveguide 11, formed on the glass substrate 12, is made from a material such as tantalum pentoxide ($TaO_5$), and is used as a transducer for a biochemical sensor. Also, the first and second diffraction gratings 13 and 14 are patterned in the glass substrate 12 through a photolithographic process to have identical structures with the same depth and pitch, and a patterned shape is transferred to the optical waveguide 11 deposited on the first and second diffraction gratings 13 and 14.

The first diffraction grating 13 is adapted to facilitate transmission of excitation light into the optical waveguide 11, while the second diffraction grating 14 is adapted to transfer the excitation light from the optical waveguide 11 to the optical detection device.

Referring to FIG. 1, the excitation light radiated from the HeNe laser 15 is reflected by the mirror 19 and incident on the lens 16. The excitation light incident on the lens 16 is spread to have a desired spot size and then is incident on the Dammann diffraction grating 17. The Dammann diffraction grating 17 divides the incident excitation light into 16 parts by minimizing an intensity of the excitation light at angles corresponding to even numbers of degrees and maximizing the intensity at angles corresponding to odd numbers of degrees.

Next, the excitation light which has been divided into 16 parts passes through the achromatic cylindrical lens 18 and is transduced into an excitation beam having 16 parallel components. Here, the Dammann diffraction grating 17 is positioned at a focus of the achromatic cylindrical lens 18, such that the excitation beam passing through the achromatic cylindrical lens 18 is aligned in parallel.

FIG. 2A is a diagram showing propagation of the excitation light through the achromatic cylindrical lens 18. FIG. 2B is a graph showing an intensity profile of the excitation light having passed through the achromatic cylindrical lens 18. FIG. 2C is a photograph of excitation light having passed through the achromatic cylindrical lens 18.

Referring again to FIG. 1, the excitation beam having 16 parallel components enters the optical waveguide 11 via the first diffraction grating 13 and propagates through the optical waveguide 11. Here, if a sample, for example, a microfluidic chip, is located on the optical waveguide 11, the excitation beam passing through the optical waveguide 11 excites the sample which then radiates light. Light radiating from the exited sample is added to the light propagating through the optical waveguide 11, and the combined light is incident on 16 microlenses via the second diffraction grating 14.

The 16 microlenses focus the incident light on the optical detection device, which comprises 16 photomulitpliers (PMTs). Also, in order to reduce interference between the beams of light incident on the 16 PMTs, the optical detection device may include a filter having 16 orifices.

The conventional optical detection device has the disadvantages of it being difficult to align the 16-part excitation beam with the 16 microlenses and to align the 16 microlenses with the 16 PMTs of the optical detector.

Also, the conventional optical detection device employs the achromatic cylindrical lens 18 to create parallel beams of light. Therefore, there is a drawback in that since the achromatic cylindrical lens 18 has a Gaussian distribution, as shown in FIGS. 2A to 2C, the intensity of the excitation light is not spatially uniform.

SUMMARY OF THE INVENTION

The present invention provides an optical detection device for biochemically analyzing samples containing microfluidic chips such as DNA chips and protein chips.

According to an aspect of the present invention, there is provided an optical detection device for detecting at least one sample, the optical detection device comprising: a light source for generating excitation light to excite the sample; a detection plate having an optical waveguide with the sample mounted thereon; a linear symmetry lens for shaping the excitation light into a desired shape having a uniform intensity distribution and transmitting it to the detection plate; and a detector for detecting radiation from the sample.

BRIEF DESCRIPTION OF THE DRAWINGS

The above and other features and advantages of the present invention will become more apparent by describing in detail exemplary embodiments thereof with reference to the attached drawings in which:

FIG. 3 is a schematic diagram of an optical detection device according to the present invention;

DETAILED DESCRIPTION OF THE INVENTION

Figure 1:
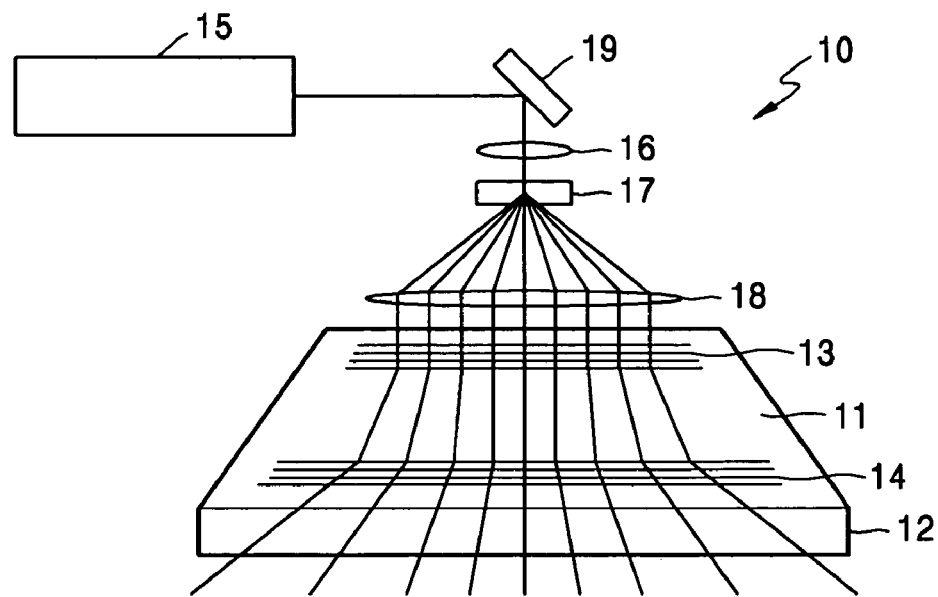
FIG. 1 is a schematic diagram of a conventional optical detection device suitable for application in the field of biochemistry.
Figure 2A:
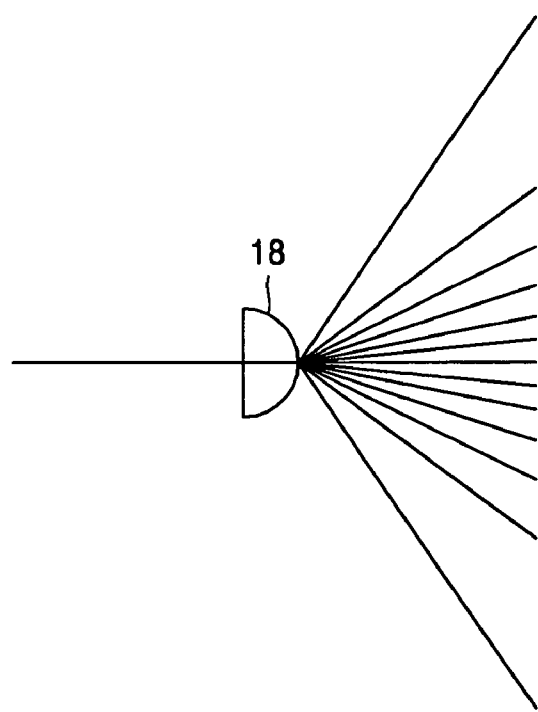
FIG. 2A is a diagram showing propagation of excitation light through an achromatic cylindrical lens.
Figure 2B:
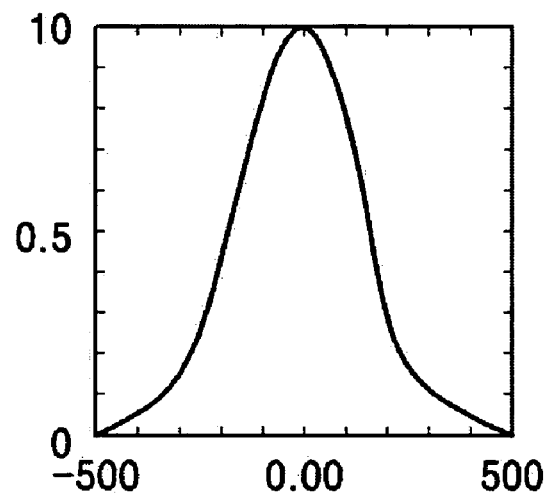
FIG. 2B is a graph showing an intensity profile of excitation light having passed through the achromatic cylindrical lens.
Figure 2C:
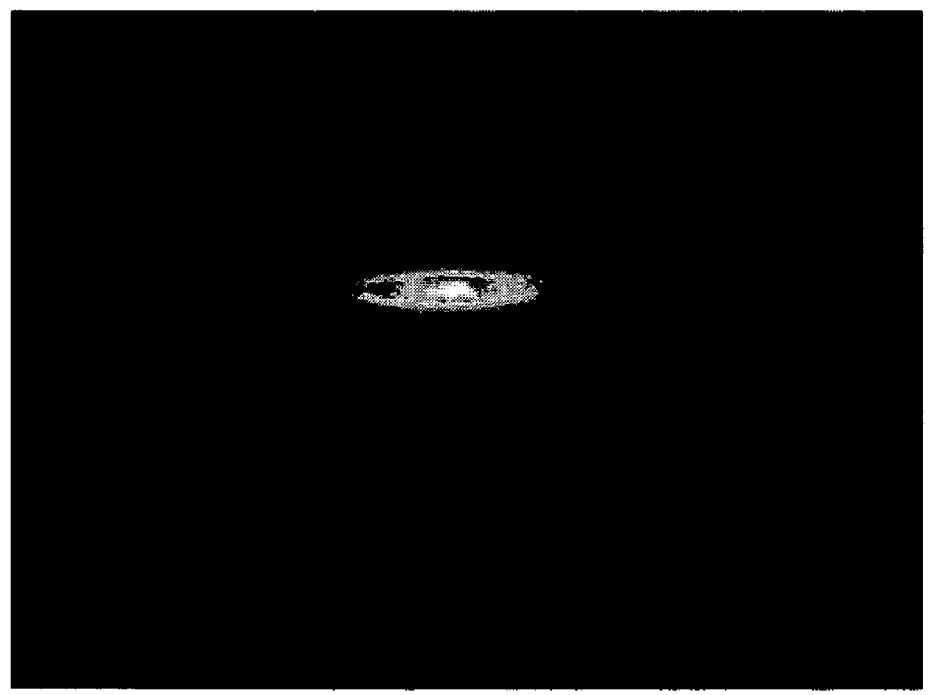
FIG. 2C is a photograph of excitation light having passed through an achromatic cylindrical lens.

An optical detection device according to embodiments of the present invention will now be described in detail with reference to the attached drawings.

FIG. 3 is a schematic diagram of an optical detection device 100 according to the present invention.

Referring to FIG. 3, the optical detection device 100 includes a light source 102 for generating excitation light, a linear symmetry lens 110, an optical fiber 104 for guiding the excitation light generated by the light source 102 to the linear symmetry lens 110, and a detection plate array 120 mounted on a transparent substrate 122.

The excitation light generated by the light source 102 is incident on the linear symmetry lens 110 through the optical fiber 104.

Figure 4A:
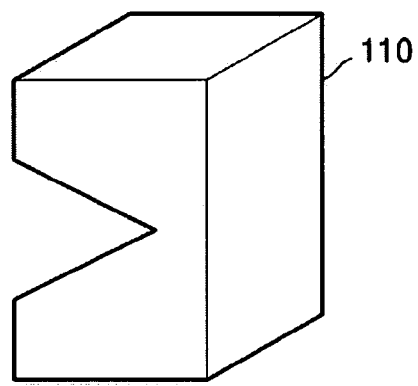
FIG. 4A is a perspective view of a linear symmetry lens according to a first embodiment of the present invention.
Figure 4B:
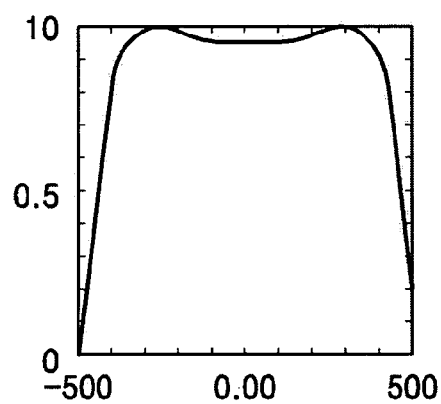
FIG. 4B is a graph showing an intensity profile of excitation light having passed through the linear symmetry lens of FIG. 4A.
Figure 4C:
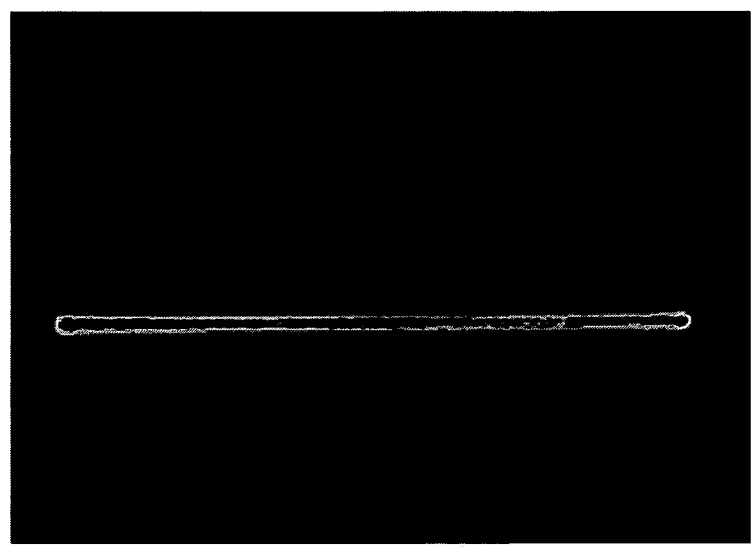
FIG. 4C is a photograph excitation light propagating through the linear symmetry lens in FIG. 4A.

FIG. 4A is a perspective view of the linear symmetry lens 110 according to a first embodiment of the present invention. FIG. 4B is a graph showing an intensity profile of the excitation light having passed through the linear symmetry lens 110 of FIG. 4A. FIG. 4C is a photograph of the excitation light having passed through the linear symmetry lens 110 of FIG. 4A.

Referring to FIGS. 4A through 4C, the linear symmetry lens 110 according to the first embodiment of the present invention is adapted to focus incident light in one direction but not in the perpendicular direction. Consequently, the excitation light having passed through the linear symmetry lens 110 has a flat line segment-shaped cross-section, as shown in FIG. 4C.

The linear symmetry lens 110 according to the first embodiment of the present invention is adapted such that excitation light passing through the linear symmetry lens has a uniform intensity distribution, as shown in FIG. 4B.

Figure 5:
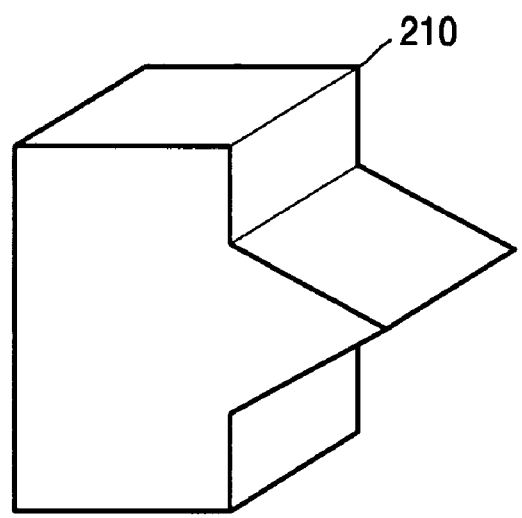
FIG. 5 is a perspective view of a linear symmetry lens according to a second embodiment of the present invention.

FIG. 5 is a perspective view of a linear symmetry lens 210 according to a second embodiment of the present invention.

Referring to FIG. 5, the linear symmetry lens 210 has a function and role substantially similar to the linear symmetry lens 110 according to the first embodiment of the present invention, except that the linear symmetry lens 210 has a convex shape.

Alternatively, although not shown in the drawings, the linear symmetry lens may have an index of refraction that varies with position in the lens, in order to form a beam with the shape shown in FIGS. 4B and 4C.

Referring again to FIG. 3, the flat beam of excitation light having a uniform intensity transmitted through the linear symmetry lens 110 is incident on the detection plate array 120.

Figure 6:
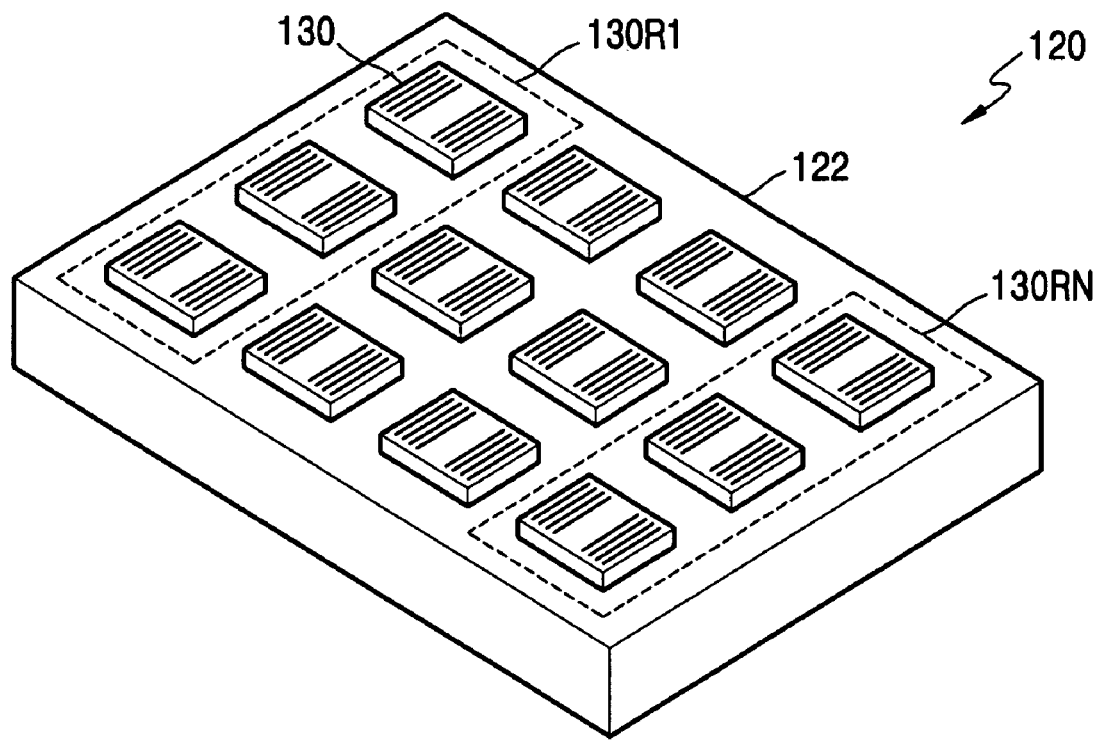
FIG. 6 is a perspective view of a detection plate array with microfluidic chips mounted thereon.
Figure 7:
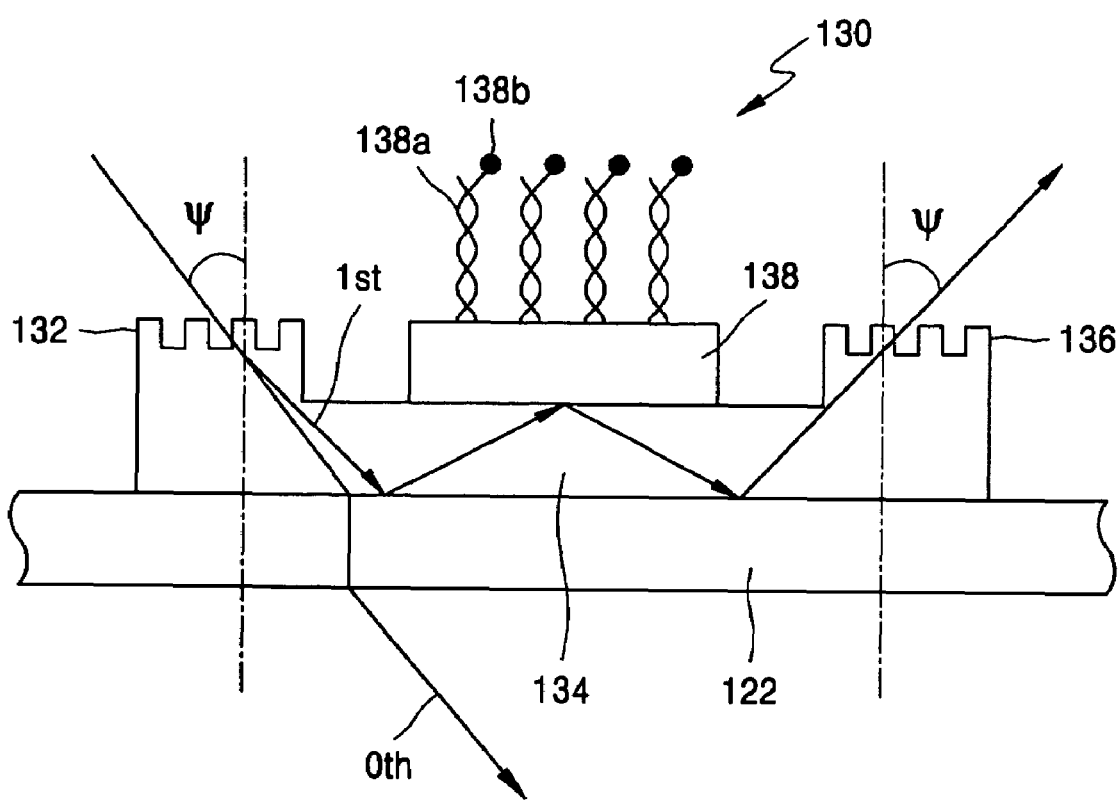
FIG. 7 is a schematic diagram of excitation light incident on a microfluidic chip mounted on a single detection plate of the detection plate array shown in FIG. 6.

FIG. 6 is a perspective view of the detection plate array 120 with microfluidic chips mounted thereon. FIG. 7 is a schematic diagram depicting excitation light incident on a microfluidic chip mounted on a single detection plate of the detection plate array 120 shown in FIG. 6.

Referring to FIGS. 6 and 7, the detection plate array 120 with microfluidic chips 138 mounted thereon includes a plurality of detection plates 130, and each of the detection plates 130 has N rows 130R1 through 130RN.

According to an embodiment of the present invention, the flat beam of excitation light having a uniform intensity formed by transmission through the linear symmetry lens 110 is preferably adapted to be the same size as first diffraction gratings formed on the first row 130R1 of each detection plate 130.

Referring to FIG. 7, if the excitation light is incident on the first diffraction grating 132 of a detection plate 130 at a desired angle $\Psi$, the excitation light is divided into $0^{th}$, $1^{st}$, $2^{nd}$, ..., $n^{th}$ diffracted beams. Preferably, the diffracted beams are aligned in such a way that the $0^{th}$ diffracted beam is transmitted to the exterior of the transparent substrate 122 and only the $1^{st}$ diffracted beam propagates through the optical waveguide 134.

The $1^{st}$ diffracted beam propagates through the optical waveguide 134 toward the second diffraction grating 136 to create an evanescent field. The evanescent field excites the sample, i.e., molecules on the surface of the microfluidic chip 138, so as to detect fluorescent light or index of refraction of the excited molecule. A biological chip, such as a DNA chip or a protein chip, may be used as the microfluidic chip 138.

For example, if the microfluidic chip 138 is a DNA chip, DNA 138a is attached to a surface of the microfluidic chip 138, and the DNA 138a is marked with a fluorescent dye 138b. Excitation of the fluorescent dye 138b generates a fluorescent beam which is detected by a detector as described below.

In the present embodiment of the present invention, the evanescent field is utilized to improve a signal-to-noise ratio. Since the evanescent field disappears at a depth of a few hundred nm from the surface of the microfluidic chip, a laser background due to surface emission is decreased and only the fluorescent beam is easily detected.

Also, the excitation light is incident on the first diffraction grating 132 and only the $1^{st}$ diffracted beam enters and propagates though the optical waveguide 134 to generate the evanescent field.

According to the present embodiment of the present invention, the optical waveguide 134 is formed from at least one of $TiO_2$, $TaO_5$, $HfO_2$, $ZrO_2$, $ZnO$, $Nb_2O_5$, and the like.

The detector for detecting the fluorescent beam is adapted to correspond to the detection plate 130 according to the embodiment of the present invention. Specifically, in order to configure the detection plate 130 in an array, the detector should be also configured in the same array. Therefore, a plurality of detectors may be arranged in a line to simultaneously detect a plurality of detection plates 130 arranged in a line. Preferably, the detector is located at a position opposite to the microfluidic chip 138 to easily detect the fluorescent beam radiated from a front surface of the detection plate with the sample, i.e., from a microfluidic chip laid thereon.

When the $1^{st}$ diffracted beam propagating through the optical waveguide 134 reaches the second diffraction grating 136, the light exits at a desired angle.

According to this embodiment of the present invention, in order to detect radiation from each of the samples, i.e., microfluidic chips 138, mounted on the detection plate array 120, the flat beam of excitation light having a uniform spatial intensity distribution is scanned in a direction perpendicular to the line shape of the first diffraction grating 132.

Also, in order to detect radiation from each of the samples, i.e., microfluidic chips 138, mounted on the detection plate array 120, the detection plate array 120 is moved in a direction perpendicular to the line shape of the first diffraction grating 132.

As described above, the present invention makes it possible to effectively detect a plurality of microfluidic chips mounted on a wide area at the same time by radiating the flat beam of excitation light having a uniform intensity to the diffraction grating using the linear symmetry lens.

In addition, by employing the linear symmetry lens, optical components can be more easily aligned compared to the conventional optical detection device employing an array of micro lenses.

While the present invention has been particularly shown and described with reference to exemplary embodiments thereof, it will be understood by those of ordinary skill in the art that various changes and modifications in form and details may be made therein without departing from the spirit and scope of the present invention as defined by the following claims.

What is claimed is:

1. An optical detection device for detecting at least one sample, the optical detection device comprising:
   a light source for generating excitation light to excite the sample;
   a detection plate having an optical waveguide with the sample mounted thereon;
   a linear symmetry lens for shaping the excitation light into a desired shape having a uniform intensity distribution and transmitting it to the detection plate; and
   a detector for detecting radiation from the sample;
   wherein:
   the detection plate is configured in an array shape;
   each of the detection plates has a first diffraction grating and a second diffraction grating;
   the excitation light shaped by the linear symmetry lens is arranged to include all first diffraction gratings laid in the same direction as line-shapes of the first diffraction grating among the detection plate arrays; and
   the light source scans in a direction perpendicular to the line-shape of the first diffraction grating to detect radiation from each of the samples mounted on the detection plate array.

2. The optical detection device of claim 1, wherein the first diffraction grating and the second diffraction grating are formed on the optical waveguide at predetermined intervals.

3. The optical detection device of claim 1, wherein the first diffraction grating and the second diffraction grating are formed in the shape of a plurality of lines.

4. The optical detection device of claim 2, wherein the excitation light shaped by the linear symmetry lens is aligned with the first diffraction grating shaped like a plurality of lines.

5. The optical detection device of claim 4, wherein the first diffraction grating transmits a first diffracted beam of the incident excitation light into the optical waveguide.

6. The optical detection device of claim 3, wherein the second diffraction grating transmits excitation light which has propagated through the optical waveguide to the outside of the optical waveguide.

7. The optical detection device of claim 1, wherein as the excitation light propagates through the optical waveguide, light generated by reaction between the excitation light and a detection material contained in the sample is detected by utilizing an evanescent field formed in a direction in which the sample is mounted.

8. The optical detection device of claim 1, wherein the sample is a microfluidic chip including a DNA chip.

9. The optical detection device of claim 1, wherein the linear symmetry lens comprises a surface of a concave triangle prism shape.

10. The optical detection device of claim 1, wherein the linear symmetry lens comprises a surface having an elongated V-shaped trench.

11. The optical detection device of claim 1, wherein the linear symmetry lens is formed by varying an index of refraction with location in the lens.

12. The optical detection device of claim 1, wherein the detection plate array moves in a direction substantially perpendicular to the line-shape of the first diffraction grating to detect radiation from each of the samples mounted on the detection plate array.

13. The optical detection device of claim 1, further comprising an optical fiber for guiding the excitation light to the linear symmetry lens.

14. The optical detection device of claim 1, wherein the optical waveguide is formed from at least one material selected from the group consisting of $TiO_2$, $TaO_5$, $HfO_2$, $ZrO_2$, $ZnO$, $Nb_2O_5$.

15. The optical detection device of claim 1, wherein if the sample is a microfluidic chip, the sample includes a fluorescent material.

16. The optical detection device of claim 15, wherein fluorescent light radiated from the fluorescent material is detected by utilizing an evanescent field formed in the optical waveguide.

* * * * *